United States Patent
Shen et al.

(10) Patent No.: US 7,838,706 B2
(45) Date of Patent: Nov. 23, 2010

(54) PREPARATION AND THE USE OF ETHOXY COMBRETASTATINS AND THEIR PRODRUGS

(75) Inventors: Weiping Shen, Shanghai (CN);
Jianping Wang, Zhejiang (CN);
Jianguo Wang, Zhejiang (CN)

(73) Assignee: Zhejiang Dade Pharmaceutical Group Co. Ltd, Zhejiang (CN)

( * ) Notice: Subject to any disclaimer, the term of this patent is extended or adjusted under 35 U.S.C. 154(b) by 0 days.

(21) Appl. No.: 12/439,783

(22) PCT Filed: May 16, 2007

(86) PCT No.: PCT/CN2007/070020

§ 371 (c)(1),
(2), (4) Date: Mar. 3, 2009

(87) PCT Pub. No.: WO2008/031333

PCT Pub. Date: Mar. 20, 2008

(65) Prior Publication Data

US 2009/0170956 A1   Jul. 2, 2009

(30) Foreign Application Priority Data

Sep. 7, 2006   (CN) .................. 2006 1 0030909

(51) Int. Cl.
C07C 237/00   (2006.01)
C07C 235/00   (2006.01)
C07C 233/00   (2006.01)
C07C 231/00   (2006.01)
A61K 31/165   (2006.01)
A61K 31/16   (2006.01)
A61K 31/66   (2006.01)

(52) U.S. Cl. ................ 568/585; 568/11; 568/15; 568/586; 568/644; 568/646; 564/158; 564/194; 564/196; 514/77; 514/114; 514/616; 514/617; 514/619; 514/620; 514/626; 514/721

(58) Field of Classification Search ............... None
See application file for complete search history.

(56) References Cited

U.S. PATENT DOCUMENTS 5,430,062 A   7/1995   Cushman et al.
5,674,906 A   10/1997   Hatanaka et al.

OTHER PUBLICATIONS

Kim et al., Chemical & Pharmaceutical Bulletin (2003), 51(5), p. 516-521.*

International Search Report of PCT/CN2007/070020, dated Aug. 2, 2007.
Pettit et al. "Isolation, Structure, and Synthesis of Combretastatins A-1 and B-1, Potent New Inhibitors of Microtubule Assembly, Derived from *Combretum caffrum*." Journal of Natural Products, vol. 50(1) Jan.-Feb. 1987, pp. 119-131.
Pettit et al. Isolation, structure, and synthesis of combretastatin A-2, A-3 and B-2. Can. J. Chem. vol. 65, 1987, pp. 2390-2396.
Pettit et al. Isolation and structure of the strong cell growth and tubulin inhibitor combretastatin A-4. Experientia, 45, 1989, pp. 209-211.
Cushman et al. "Synthesis and Evaluation of Analogues of (Z)-1-(4-Methoxyphenyl)-2-(3,4,5-thrimethoxyphenyl)ethane as Potential Cytotoxic and Antimitotic Agents." Journal of Medicinal Chemistry, cil 35(12), 1992, pp. 2293-2307.
Pettit et al. Antineoplastic Agents. 291. Isolation and Synthesis of Combretastatins A-4, A-5, and A-6. J. Med. Chem., 38, 1995. pp. 1666-1672.
Thorpe. "Vascular Targeting Agents as Cancer Therapeutics." Clinical Cancer Research, vol. 10, Jan. 15, 2004, pp. 415-427.
West et al. Combretastatin A4 phosphate. Anit-Cancer Drugs, vol. 15(3), 2004. pp. 179-187.
Young et al. "Combretastatin A4 phosphate: background and current clinical status." Expert Opin. Investig. Drugs vol. 13(9), 2004, pp. 1171-1182.

* cited by examiner

*Primary Examiner*—Brian J Davis
(74) *Attorney, Agent, or Firm*—Hamre, Schumann, Mueller & Larson, P.C.

(57) ABSTRACT

The invention disclosed a total synthesis process of novel ethoxy combretastatins and their prodrugs. Combretastatins are chemically modified by ethoxy substituted on the 4'-position of their B aryl ring and are converted to be their soluble prodrugs of phosphate or their inner salt of phosphorylcholine by modifying the hydroxyl on the 3'-position of their B aryl ring. Similarly, 3'-amino combretastatin is 4'-ethoxy chemically modified and further side chain of amino acid can be introduced to the amino to form soluble prodrug of amino acidamide. The structure of the said compound is showed as formula (I). Ethoxy combretastatins possess potent tubulin polymerization inhibitory activity and can be used for the treatment of inhibiting tumor or neovascular.

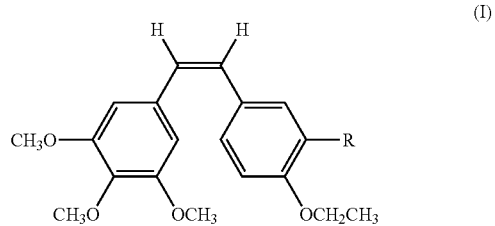

(I)

9 Claims, 2 Drawing Sheets

PREPARATION AND THE USE OF ETHOXY COMBRETASTATINS AND THEIR PRODRUGS

FIELD OF THE INVENTION

The present invention is directed to the field of pharmaceutical synthesis, especially to the synthesis of anti-cancer medicament.

BACKGROUND ARTS

Combretaceae, a family of shrubs and trees found in tropical or subtropical areas, is well represented in traditional medical practices. Twenty-five species in *Combretum*, which is a genus in Combretaceae, are known to be used for treating Hansen's disease and cancers in Africa and India. However, only a few of them, such as *Combretum micrantbum* and *Combretum zeyberi*, have been studied. *Combretum caffrum*, a species of *Combretum*, is called Mdulu in South Africa by the Zulus, while is also known as Bushveld willow, Bushwill, or Rooiblaar elsewhere. At the end of 1970s, after widespread screening, National Cancer Institute found that the *Combretum* genus plants can strongly inhibit the P388 lymphocytic leukemial cell. Since the beginning of 1980s, a wide interest in studying this kind of plant has been caused. During this period, Dr. G. Robert Pettit, the director of Cancer Research Institute of Arizona State University, and his four colleagues isolated combretastatins from the African willow tree *Combretum caffrum* which has been used by the Zulus as herbal remedies and as paint for spears. In the *Journal of Canadian Chemistry*, Dr. George R. Pettit stated that the bark of the tree had anti-tumor activity. Afterward, not only many compounds having high activity are isolated and identified, but also the research on their pharmacological mechanism and modifications of their structures have been developed. (Pettit, G. R.; et al. 1) *Can. J. Chem.* 1987, 65, 2390-2396. 2) *J. Nat. Prod.* 1987, 50, 119-131. 3) *Experieutia* 1989, 45, 209-211.) Combretastatins are a series of compounds characterized by the structure of Z-1,2-diphenyl ethylene. Among those compounds, Combretastatin A-4 [CA-4, Combretastatin, (Z)-1-(3,4,5-trimethoxy)phenyl-2-(3'-hydroxy-4'-methoxy)phenylethylene] proves to be exceptionally strong inhibitor of tubulin polymerization, and is represented by formula XVII (Pettit, G. R., et al. *J. Med. Chem.* 1995, 38, 1666-1672).

R = OH, CA-1
R = H, CA-4

Recently, CA-4 shows exciting property in shutting down tumor vasculature as a tumor vascular targeting agent. (Thorpe, P. E. *Clin. Cancer Res.* 2004, January 15, 10(2), 415-427. West, C. M. Price, P. *Anticancer Drugs.* 2004, March, 15(3), 179-187. Young, S. L.; Chaplin, D. J. *Expert Opin. Investig. Drugs.* 2004, September, 13(9), 1171-1182.) CA-4 developed by Oxigene Inc., USA as a new anticancer drug has entered phase III clinical trial. In 1997, T. Hatanaka, et al. in Ajinomoto Co., Japan discovered that if the 3'-hydroxyl of CA-4 was replaced by amino group and then modified as amino amide, the anticancer activity of the obtained water-soluble prodrug could be greatly improved while with much less toxicity compared to CA-4 (U.S. Pat. No. 5,674, 906). At present, 3'-amino CA-4 amino amide (AVE8062) developed by Aventis Pharma Co., France has entered phase II clinical trial.

Therefore, looking for new combretastatins with higher activity is an exigent task in this field.

SUMMARY OF THE INVENTION

A object of the invention is to provide ethoxy combretastatins of formula I.

Another object of the invention is to provide a method for producing the compounds of formula I.

Another object of the invention is to provide a pharmaceutical composition containing the compounds of formula I.

Another object of the invention is to provide the medical use of the compounds of formula I.

In the first aspect, the present invention provides compounds of formula I:

wherein:

R is hydroxyl, amino, nitro, halogen, alkoxy, phosphoric acid, phosphorylcholine, or side chain of an amino acid, and its pharmaceutically acceptable salts.

In a preferred embodiment, R is hydroxyl, amino, phosphoric acid, phosphorylcholine, or side chain of an amino acid, and its pharmaceutically acceptable salts.

In a preferred embodiment, R is hydroxyl, amino, disodium or ammonium phosphate or inner salt of phosphorylcholine, —NH(COCHR'NH)$_m$—H; wherein R' is hydrogen, side chain of a natural amino acid, phenyl; m is an integer of 1 to 3.

In a preferred embodiment, R is —OH, —NH$_2$, —OPO$_2$Na$_2$, —OPO$_3$CH$_2$CH$_2$NMe$_3$, —NHCOCH$_2$NH$_2$, —NHCOCHNH$_2$CH$_2$OH.

In the second aspect, the invention provides a method for preparing the compounds of formula I, comprising the steps of:

(1) Under phase-transfer catalyst conditions, 4-hydroxy-3-methoxybenzaldehyde II is ethylated with ethyl bromide to synthesize 4-ethoxy-3-methoxybenzaldehyde represented by formula III;

(2) Using lithium diphenylphosphine, selectively replacing m-methyl of 4-ethoxy-3-methoxybenzaldehyde III with hydroxyl to synthesize 4-ethoxy-3-hydroxybenzaldehyde represented by formula IV;

(3) With hydroxyl being protected, 4-ethoxy-3-hydroxybenzaldehyde VI is reacted with 3,4,5-trimethoxybenzyltriphenylphosphonium ylid via Wittig reaction, and then the resulting compound is deprotected to obtain ethoxy combretastatin represented by formula VI;

(4) Ethoxy combretastatin VI is phosphorylated with phosphoryl reagent to synthesize its phosphate derivatives;

(5) Under alkaline conditions, phosphate derivatives of ethoxy combretastatin are converted to ethoxy combretastatin phosphate or inner salt of phosphorylcholine.

In a preferred embodiment, the phosphoryl reagent in step (4) is selected from the group consisting of dibenzyl phosphite or 2-chloro-1,3,2-dioxaphospholane.

In a preferred embodiment, the m-hydroxyl in step (3) is protected by trityl chloride.

In a preferred embodiment, (Z)-1-(3,4,5-trimethoxy)phenyl-2-(3'-trityloxy-4'-ethoxy) phenylethylene in step (3) is reacted with concentrated hydrochloric acid and trifluoroacetic acid to remove trityl and give ethoxy combretastatin VI.

In a preferred embodiment, the phosphate derivative of ethoxy combretastatin in step (5) being converted to ethoxy combretastatin phosphate prodrug via cracking reactions under alkaline conditions, pH=8-10 is preferred.

In a preferred embodiment, the phosphate derivative of ethoxy combretastatin in step (5) is reacted with tertiary amine to produce the prodrug, inner salt of phosphorylcholine.

In a preferred embodiment, the present invention provides a method for preparing the compounds of formula I, comprising the steps of:

(a) Under phase-transfer catalyst conditions, 4-hydroxy-3-nitrobenzaldehyde IX is ethylated with ethyl bromide to synthesize 4-ethoxy-3-nitrobenzaldehyde represented by formula X;

(b) Under 254 nm ultraviolet photocatalysis, 4-ethoxy-3-nitrobenzaldehyde X is reacted with 3,4,5-trimethoxybenzyltriphenylphosphine ylid via Wittig reaction to obtain (Z)-1-(3,4,5-trimethoxy)phenyl-2-(3'-nitro-4'-ethoxy) phenylethylene, which is represented by formula XI;

(c) (Z)-1-(3,4,5-trimethoxy)phenyl-2-(3'-nitro-4'-ethoxy) phenylethylene XI is reduced with reducing agents to give 3'-amino ethoxy combretastatin XII;

(d) 3'-amino ethoxy combretastatin XII is reacted with amino acid derivatives to give corresponding amino amide derivatives.

(e) Under alkaline conditions, the above mentioned amino amide derivatives are converted to 3'-amino ethoxy combretastatin amino amides.

In a preferred embodiment, reducing agents in step (c) are selected from the group consisting of stannous chloride, Zinc powder/acetic acid, sodium thiosulfate, nickel chloride/sodium borohydride.

In a preferred embodiment, in step (d), under catalysis of dicyclohexylcarbodiimide (DCC) and 1-hydroxy benzotriazole (HOBt) or Benzotriazol-1-yl-oxytris(dimethylamino) phosphonium hexafluorophosphate (BOP), (Z)-1-(3,4,5-trimethoxy)phenyl-2-(3'-amino-4'-ethoxy)phenylethylene is reacted with N-α-9-fluorylmethoxycarbonyl amino acid derivatives (FmocAA) to change 3'-amino into Fmoc-amino amide.

In a preferred embodiment, (Z)-1-(3,4,5-trimethoxy)phenyl-2-(3'-amino-4'-ethoxy)phenylethylene Fmoc-amino amide in step (e) is converted to 3'-amino ethoxy combretastatin amino amide water-soluble prodrugs by removing Fmoc, the preferred alkaline condition is sodium hydroxide aqueous solution.

In the third aspect, the invention provides a pharmaceutical composition comprising an effective amount of the compounds of formula I and pharmaceutically acceptable carrier.

In another preferred embodiment, the said pharmaceutical compositions can be administered orally or intravenously in the following medicament forms: freeze-dried powder, powder, granule, tablets, capsule, syrup, suppository, injection, emulsion, tincture, suspension, or solution.

In the forth aspect, the invention provides the use of the compounds of formula I for the manufacture of a tubulin-binding inhibitor.

In the fifth aspect, the invention provides the use of the compounds of formula I for the manufacture of a medicament for the treatment of the diseases caused by abnormal angiogenesis.

In another preferred embodiment, the compounds of formula I are used to treat various tumors growth and metastasis caused by abnormal angiogenesis. Said tumors include, but not limited to the following: lung carcinoma, non small cell lung carcinoma, hepatocarcinoma, adenocarcinoma of pancreas, carcinoma of stomach, osteocarcinoma, esophagus carcinoma, breast cancer, prostate cancer, carcinoma of testis, colon carcinoma, ovarian cancer, bladder carcinoma, cervix cancer, melanocarcinoma, squamous cell carcinoma, basal cell carcinoma, adenocarcinoma, sweat gland carcinoma, sebaceous gland carcinoma, papillary carcinoma, papillary adenocarcinomas, cystadenocarcinoma, cystocarcinoma, medullary carcinoma, bronchogenic carcinoma, osteocyte carcinoma, epithelial carcinoma, bile duct carcinoma, embryonal carcinoma, choriocarcinoma, seminoma, Wilms' tumor, spongiocytoma, astrocytoma, medulloblastoma, craniopharyngioma, ependymoma, pinealoma, hemangioblastoma, acoustic neuroma, meningioma, neuroblastoma, optic nerve blastoma, retinoblastoma, neurofibroma, fibrosarcoma, fibroblastoma, fibroma, fibroadenoma, fibrochondroma, fibrocystoma, fibromyxoma, fibro-ostroma, fibromyxosarcoma, fibropapilloma, myxosarcoma, myxocystoma, myxoenchondroma, myxochondeosarcoma, myxochondrofibrosarcoma, myxoadenoma, myxoblastoma, liposarcoma, lipoma, lipoadenoma, lipoblastoma, lipochondroma, lipofibroma, lipoangioma, myxolipoma, chondrosarcoma, chondroma, chondromyoma, chordoma, chorioadenoma, chorioepithelioma, chorioblastoma, osteosarcoma, osteoblastoma, osteochondrofibroma, osteochondrosarcoma, osteochondroma, osteocystoma, osteodentinoma, osteofibroma, fibrosarcoma of bone, angiosarcoma, angioma, angiolipoma, hematal chondroma, angioblastoma, angiokeratoma, angioglioma, hemangioendothelioma, hemangiofibroma, angiomyoma, angiolipoma, hematal lymphangioma, angiolipoleiomyoma, angiomyoliopma, angiomyoneuroma, angiomyxoma, angioreticuloendothelioma, lymphangiosarcoma, lymphogranulomatosis, lymphangioma, lymphoma, lymphomyxoma, lymphosarcoma, lymphangiofibroma, lymphocytoma, lymphoepithelioma, lymphoblastoma, endothelial carcinoma, endoblastoma, synovioma, synoviosarcoma, mesothelioma, mesocytoma, Ewing's tumor, liomyoma, leiomyosarcoma, leiomyoblastoma, liomyofibroma, rhabdomyoma, rhabdomyosarcoma, rhabdomyomyxoma, acute lymphocytic leukemia, acute myelocytic leukemia, chronic leukemia, polycythemia vera, lymphoma, multiple myeloma.

In another preferred embodiment, the compounds of formula I are used to treat other related diseases which are aroused by pathological angiogenesis, which include but not limited to the following: rheumatoid arthritis, diabetic retinopathy, retinopathy of prematurity, retinal vein obstruction, psoriasis, acne rosacea, Kaposi sarcoma, atopic keratitis, epidemic keratoconjunctivitis, neovascular glaucoma, bacterial ulcers, fungal ulcers, Herpes simplex infections, Herpes zoster infections, protozoan infections, *Mycobacterium* infections, polyarteritis, sarcoidosis, scleritis, flush, Sjogren's disease, systemic lupus, Acquired Immune Deficiency Syndrome (AIDS), syphilis.

Hereby, the present invention provides some new derivatives of Combretastin with further improved biological activities.

BRIEF DESCRIPTION OF THE DRAWINGS

wherein.

PTC represents phase-transfer catalyst; Cat. represents catalyst; Wittig reaction; $Ph_2PLi$ represents Lithium diphenylphosphine; n-BuLi represents normal butyl lithium; TFA represents trifluoroacetic acid; i-$Pr_2$EtN represents diisopropylethylamine; $(PhCH_2O)_2P(O)H$ represents dibenzyl phosphate; TMBS represents trimethylbromosilane; Fmoc-L-Ser represents N-α-9-fluorenylmethoxycarbonyl-L-serine derivative; Fmoc-Gly represents N-α-9-fluorenylmethoxycarbonyl-glycine derivative; BOP represents Benzotriazol-1-yl-oxytris(dimethylamino)phosphonium hexafluorophosphate; DCC represents cyclohexylcarbodiimide; HOBt represents 1-hydroxybenzotriazole; DMF represents dimethylformamide; $NMe_3$ represents trimethylamine; aq. NaOH represents a diluted sodium hydroxide aqueous solution; conc. HCl represents concentrated hydrochloric acid.

DETAILED DESCRIPTION OF THE INVENTION

Through extensive and intensive study, the inventors unexpectedly discovered that the 4' position of B-ring of the nature product Combretastatin is an active site, and that the original methoxy group at the 4' position of B-ring of Combretastatin can be replaced by an ethoxy group to improve the targeting activity of tumor vascular.

The above mentioned nature product Combretastatin was successfully introduced an ethoxy group in the 4' position of B aromatic ring by means of the key reaction of demethylation using lithium diphenylphosphine selectively.

Meanwhile, 254 nm ultraviolet photocatalysis was used in synthesizing those compounds via Wittig reaction, which improved stereoselectivity of the reaction, thus making the yield of products in Z configuration increase substantially.

These new compounds possess enhanced ability of tubulin polymerization inhibition, which can be used for treating tumor and a pathological state caused by abnormal angiogenesis.

Compounds

The present invention provided new derivatives of Combretastatin in which 4' position of B aromatic ring was introduced an ethoxy group while 3' position mainly was a hydroxyl group with its derived phosphate or inner salt of phosphorylcholine and an amino group with its derived amino amide water-soluble prodrugs, represented by Formula I R is hydroxyl, amino, nitro, halogen, alkoxy, phosphate, inner salt of phosphorylcholine, side chain of an amino acid, or its pharmaceutically acceptable salts.

When R is selected as phosphate, inner salt of phosphorylcholine, side chain of an amino acid, or its pharmaceutically acceptable salts, its water-soluble prodrugs are formed.

When R is hydroxyl, water-soluble prodrugs, phosphate or inner salt of phosphorylcholine, are derived.

When R is amino, water-soluble prodrugs, —NH(COCHR'NH)$_n$—H (in which R' is a side chain of a natural amino acid) are derived.

Preferably, ethoxy combretastatin has priority when R is hydroxyl; 3'-amino ethoxy combretastatin has priority when R is amino. The structure is represented by formula I, wherein R=—OH, —NH$_2$, —OP(O)(ONa)$_2$, —OP(O)(O$^-$)(OCH$_2$CH$_2$NMe$_3$), —NH(COCHR'NH)$_m$—H (wherein R' is hydrogen, side chain of a natural amino acid, phenyl; m is an integer of 1 to 3).

The ethoxy combretastatins of the present invention can form pharmaceutically acceptable base-addition salts with inorganic bases or organic bases. The mentioned inorganic bases include but not limited to potassium hydroxide and ammonium hydroxide, while the mentioned organic bases include, but not limited to, aliphatic amines (such as triethylamine), hydroxylamine (such as ethanol amine), amino acids (such as histidine), amino glycosides (such as neoamine).

The ethoxy combretastatins of the present invention can form pharmaceutically acceptable acid-addition salts with inorganic acids or organic acids. The mentioned inorganic acids include but not limited to hydrochloric acid, sulfuric acid and phosphoric acid, while the mentioned organic acids include, but not limited to, oxalic acid, fumaric acid, maleic acid, malic acid, citric acid, tartaric acid and glutamic acid.

Preparations of Compounds

The present invention provides a process for the preparation of compounds of formula I comprising the following steps:

With the presence of the phase transfer catalyst, 4-hydroxy-3-methoxybenzaldehyde was ethylated and selectively demethylated into a series of novel p-ethoxybenzaldehyde derivatives by using lithium diphenylphosphine. The above compounds of p-ethoxybenzaldehyde derivatives then underwent Wittig reaction as raw materials with high stereoselectivity, thus giving a series of ethoxy combretastatins derivatives, followed by phosphatization, or combining with amino acids etc. to obtain a series of water-soluble prodrugs of ethoxy combretastatin.

Synthesis of p-ethoxybenzaldehyde Derivatives

4-ethoxy-3-methoxybenzaldehyde III or 4-ethoxy-3-nitrobenzaldehyde X was prepared by 4-hydroxy-3-methoxybenzaldehyde (vanillin) II or 4-hydroxy-3-nitrobenzaldehyde IX using ethyl bromide in the presence of inorganic base and phase transfer catalyst.

The above mentioned inorganic bases were selected from the group consisting of: hydroxide, one or more of carbonates, preferably from the group consisting of potassium hydroxide and/or potassium carbonate. The mentioned phase transfer catalyst were selected from the group consisting of quarternary ammonium salts, quarternary phosphonium salts, crown ether, polyethyleneglycol (PEG), preferably from the group consisting of benzyltriethyl ammonium chloride, tetrabutyl ammonium bisulphate (TBAB), 18-crown-6, diphenyl-18-crown-6, dicyclohexyl-18-crown-6 ethers or PEG-400.

The formyl group of 4-ethoxy-3-methoxybenzaldehyde III was protected by using glycol compounds, and then the 3-position methoxy was selectively demethylated with lithium diphenylphosphine to obtain 4-ethoxy-3-hydroxybenzaldehyde IV.

IV

Synthesis of Ethoxy Combretastatin

In the presence of organic base catalyst, 4-ethoxy-3-hydroxybenzaldehyde IV was reacted with triphenylmethyl chloride to obtain 3-triphenymethoxy-4-ethoxybenzaldehyde. 3,4,5-trimethoxybenzyltriphenyl phosphine bromide was converted into corresponding phosphonium ylide with n-butyl lithium, and then the corresponding phosphonium ylide was reacted with the above 3-triphenymethoxy-4-ethoxybenzaldehyde via Wittig reaction to form the cis-stilbene derivatives with high efficiency. Subsequently, the trityl group was deprotected with the combination action of concentrated hydrochloric acid and trifluoroacetic acid to obtain ethoxy combretastatin VI.

V

VI

The above mentioned inorganic bases were selected from the group consisting of triethylamine, diisopropylethylamine.

Synthesis of 3'-amino Ethoxy Combretastatin

Catalyzed by 254 nm ultraviolet light, 4-ethoxy-3-nitrobenzaldehyde X was reacted with above mentioned phosphonium ylide via Wittig reaction to obtain (Z)-3'-nitro ethoxy combretastatin XI with high selectivity. Then the 3'-nitro was reduced to amino group by reducing agents. Among the reducing agents, stannous chloride, Zinc powder/acetic acid, sodium thiosulfate, nickel chloride/sodium borohydride were preferred. Thus, 3'-amino ethoxy combretastatin XII was obtained.

XI

XII

Synthesis of Ethoxy Combretastatin Phosphate

Figure 1:
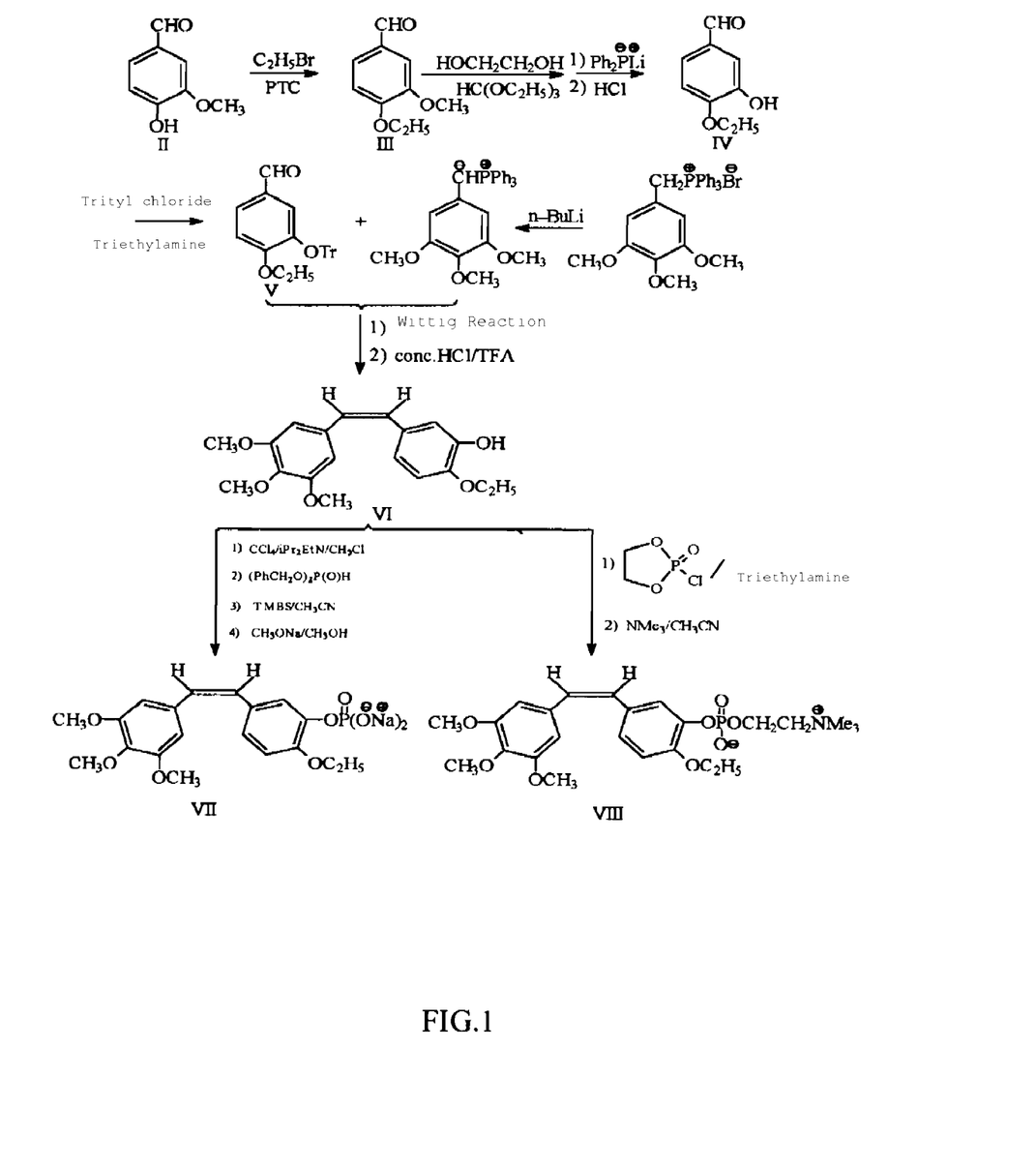
FIG. 1: synthetic route of ethoxy combretastatin and its water-soluble prodrugs.

As shown in FIG. 1, the 3'-position hydroxyl of above ethoxy combretastatin VI was converted to phosphate disodium salt by reacting with carbon tetrachloride, diisopropylethylamine, dibenzyl phosphite, trimethylsilane bromide, sodium methoxide, thus obtaining ethoxy combretastatin phosphate VII.

VII

Synthesis of Ethoxy Combretastatin Phosphorylcholine

Alternatively, also shown in FIG. 1, the 3'-position hydroxyl of above ethoxy combretastatin VI was converted to cyclic phosphate derivative of ethoxy combretastatin by reacting with 2-chloro-1,3,2-dioxaphospholane, a kind of phosphoryl reagent. With the presence of trimethylamine, the ring of the cyclic phosphate derivative opened to give inner salt of ethoxy combretastatin phosphorylcholine VIII.

VIII

Synthesis of 3'-amino Ethoxy Combretastatin Amino Amide

Figure 2:
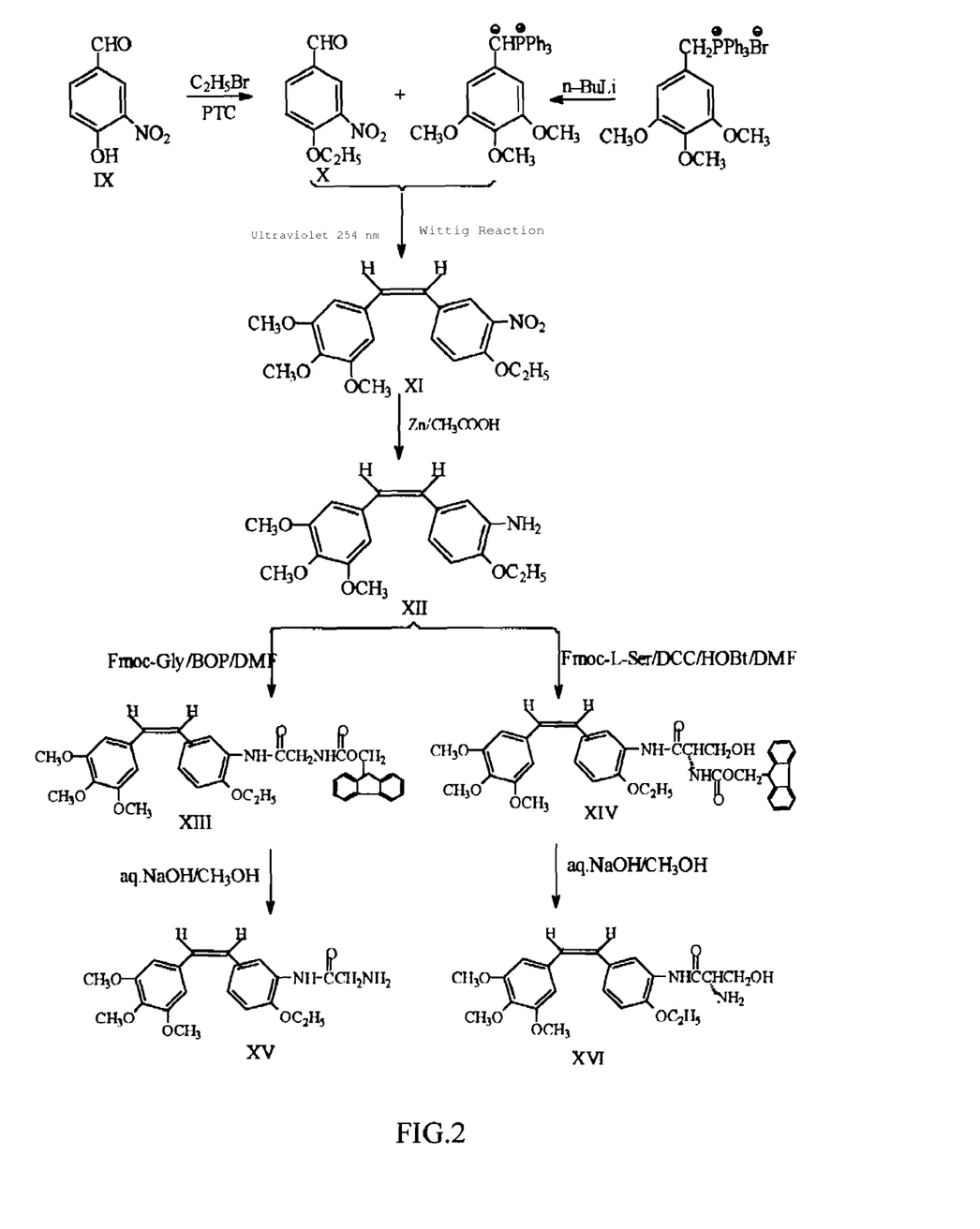
FIG. 2: synthetic route of 3'-amino ethoxy combretastatin and its amino amide derivatives.

As shown in FIG. 2, 3'-amino ethoxy combretastatin XII was treated with N-α-9-fluorenylmethoxycarbonyl amino acid derivative (FmocAA) and BOP reagent, or cyclohexylcarbodiimide (DCC) and 1-hydroxybenzotriazole (HOBt) to introduce an amino acid side chain at the 3'-amino group, as represented by XIII and XIV. Subsequently, the product having an amino acid side chain at the 3'-position was deprotected with sodium hydroxide and turned to amino amide to obtain a series of 3'-amino ethoxy combretastatin amino amide derivatives, as represented by XV and XVI.

Pharmaceutical Compositions

The pharmaceutical composition of the invention contains therapeutic effective amount of compounds of formula I and the pharmaceutical acceptable carrier, in which the amount of the compounds of formula I may range from 0.1% to about 99% (w/w) of the compositions. The said pharmaceutical compositions may present in various dosage forms. These compositions could be administered orally or intravenously and could be formulated into the following dosage forms: freeze-dried powder, granule, powder, tablets, capsule, syrup, suppository, injection, emulsion, tincture, suspension, or solution.

For intravenous administration, the compositions could be formulated into freeze-dried powder, which was dissolved with saline or glucose solution.

For oral administration, the compositions could be formulated into tablet, lozenge, capsule, pill, powder, granule, paste, suspensions, emulsion or solutions.

The dosage of the active ingredient may vary with the mode of administration and the severity of diseases to be treated. Generally, when the compound of the present invention was taken by a daily dosage ranging from about 0.5 mg/kg body weight to about 500 mg/kg body weight per day, it may create a satisfactory treatment efficacy. In one preferred embodiment of the present invention, the present compound is administered to the subject in divided doses between 2 and 4 times per day, or administered as extended-release forms. For most of the large-scale mammals, the total daily dosage may range from 1 mg to about 100 mg. The suitable oral administration dosage forms contain about 0.5 to about 500 mg of active ingredient and mixed with solid or liquid form of pharmaceutical acceptable vehicle. The dosage is adjustable for the most preferred treatment response. For example, according to different therapeutic conditions, the present compositions can be administrated daily in divided doses, or can be administrated scaling down. Generally, the suitable clinical oral administration dosage for an adult may range from 1 mg to about 1000 mg, and preferably from about 10 mg to about 200 mg. Non-oral administration dosage for an adult may range from 0.1 mg to about 100 mg, and preferably from about 1 mg to about 100 mg.

The ethoxy combretastatins of the present invention which were prepared by the above-mentioned methods can be administered either orally or intravenously when it is used as vascular targeting agent. The dosage of the active ingredient may vary with the severity of diseases. The daily dosage usually may range from 1 mg to about 3,000 mg for an adult.

In a preferred embodiment, compounds of the present invention may be administered orally or intravenously. The solid carriers include starch, lactose, calcium hydrogen phosphate, crystalline cellulose, sugar and kaolin; and the liquid carriers include sterile water, polyethylene glycol, mannitol, nonionic surfactant and edible oil (such as corn oil, peanut oil and sesame oil), which are suitable for the characteristic of the active ingredients and appropriate for specific administration mode. The excipients which are commonly used in the preparation of pharmaceutical compositions can also advantageously incorporated with, for example, flavoring, pigment, preservative and antioxidant, such as Vitamin E, Vitamin C, BHT and BHA.

As cited in the specification, intravenous administration, including intraperitoneal injection and drip fluid infusion, may also be carried out with freeze-dried powder which can be dissolved with saline or glucose solution. The freeze-dried powder could be prepared by the routine method in the art.

Compositions of the invention can be formulated into oral preparations, including tablets and capsules. The preparations may be prepared by mixing the effective ingredient and at least one of pharmaceutically acceptable additives, including excipient, binder, disintegrant, lubricant, colorant, correctant and the like, and the resulting mixture may be formulated into powder, granules, tablets, coated tablet, pills, capsules or the like. Examples of suitable excipients may include one or more of lactose, corn starch, saccharide, dextrose, sorbitol, and crystalline cellulose. Examples of suitable binders may include one or more of polyvinyl alcohol, ethyl cellulose, methyl cellulose, gum Arabic, tragacanth, gelatin, shellac, hydroxypropyl cellulose, hydroxypropyl starch, and polyvinyl pyrrolidone. Examples of disintegrants may include one or more of starch, agar, gelatin powder, crystalline cellulose, calcium carbonate, sodium bicarbonate, calcium citrate, cyclodextrin, and pectin. Examples of appropriate lubricants may include one or more of magnesium stearate, talc, polyethylene glycol, silica, and hardened vegetable oil. Examples of colorants may include those which have been approved for pharmaceutical use. Examples of acceptable correctants may include coco powder, menthol, peppermint oil, refined borneol, and cinnamon. The tablets or granules can be coated with sugar, gelatin and etc. if necessary. These medicaments can also contain other additives, including inert diluent, preservative such as p-hydroxybenzoates and sorbic acid, antioxidant such as α-Vitamin E, Vitamin C and cysteine, decomposition agent, adhesive agent, thickening agent, buffer solution, sweetening agent, flavoring agent and perfume. Tablets and pills can also be coated with enteric coating. The liquid forms of oral administration may include emulsion, syrup, tincture, suspension and solution, which can contain commonly-used inert diluents such as water.

The main advantage of the invention is introducing ethoxy at 4' position of B aromatic ring of nature product of Combretastatin to improve its targeting activity toward tumor vascular.

The invention is further illustrated by the following examples. These examples are only intended to illustrate the invention, but not to limit the scope of the invention. For the experimental methods in the following examples, the methods are is performed under routine conditions, or as instructed by the manufacturers except for those specifically indicated. All parts, percents, rations are by weight, unless otherwise specified.

Example 1

Synthesis of 4-ethoxy-3-methoxybenzaldehyde

A 1-liter four-necked flask fitted with thermometer, mechanical stirrer, and reflux condenser was charged with 62 g 4-hydroxy-3-methoxybenzaldehyde (0.41 mol) and 400 ml isopropyl alcohol. The mixture was stirred for 20 min, and then a 120 ml water solution containing 5 g 18-crown-6 ether and 106.3 g sodium hydroxide (2.66 mol) was gradually dropped thereto using a constant pressure funnel. After dropping, the mixture was stirred for 30 min, and then heated to 60° C. At this temperature, 67.3 g ethyl bromide (0.62 mol) was introduced within 5-6 hours and the reaction was monitored with TLC. After the reaction finished, the mixture was cooled to 15° C., and 400 ml water was then added to quench the reaction. The resulting mixture was extracted three times with ether (300 ml×3). The organic layer was washed with water to pH=7, and dried with anhydrous magnesium sulfate. Part of the ether was removed by flash distillation and then large amount of petroleum ether was added to precipitate crude product. The crude product was recrystallized from diethyl ether/petroleum ether to give 67 g 4-ethoxy-3-methoxybenzaldehyde in a yield of 91%. $^1$H-NMR (ppm) δ: 9.87 (1H, s; —CHO); 7.31 (1H, m; 2-ArH); 7.26 (1H, m; 6-ArH); 6.86 (1H, m; 5-ArH); 3.98 (2H, q; —CH$_2$); 3.73 (3H, s; —OCH$_3$); 1.42 (3H, t; —CH$_3$). MS (m/Z): 180 (M$^+$).

Example 2

Synthesis of 4-ethoxy-3-nitrobenzaldehyde

This example was according to Example 1, except that 4-hydroxy-3-methoxybenzaldehyde was replaced by 68.5 g 4-hydroxy-3-nitro-benzaldehyde (0.41 mol) to obtain 68.7 g 4-ethoxy-3-nitrobenzaldehyde in a yield of 86%. $^1$H-NMR (ppm) δ: 9.96 (1H, s; —CHO); 7.73 (1H, m; 2-ArH); 7.58 (1H, m; 6-ArH); 7.33 (1H, m; 5-ArH); 4.15 (2H, q; —CH$_2$); 3.82 (3H, s; —OCH$_3$); 1.53 (3H, t; —CH$_3$). MS (m/Z): 195 (M$^+$).

Example 3

Synthesis of 4-ethoxy-3-hydroxybenzaldehyde

Step 1: In argon atmosphere, 54 g 4-ethoxy-3-methoxybenzaldehyde (0.3 mol), 130 g ethylene glycol (2.1 mol) and 133 g triethyl orthoformate (0.9 mol) were charged into a three-necked flask successively. The mixture was heated to reflux at about 100° C., and then 1 ml boron trifluoride ether solution was added as catalyst. The mixture was reacted for 24 hours, monitored with TLC. The mixture was then cooled to room temperature, and 200 ml 15% aqueous sodium hydroxide solution was added. The mixture was extracted with 300 ml diethyl ether. The extract was washed with saturated brine, dried with anhydrous magnesium sulfate, distilled under reduced pressure to remove ethylene glycol and triethyl orthoformate, and then give yellow oily product.

Step 2: A 200 mL solution of 1.28M lithium diphenylphosphine in tetrahydrofuran was charged in a flask, 56 g above-prepared acetal (0.25 mol) was added in portions. After addition, the resulting mixture was stirred for 3-4 hours under room temperature, monitored with TLC. Water was added to quench the reaction, and then 200 ml 30% aqueous sodium hydroxide solution was added. The mixture was extracted with 300 ml diethyl ether. The water layer was cooled and acidified with hydrochloric acid to pH=3-4, and then was extracted with 500 ml diethyl ether. The ether extracts was combined and washed with saturated brine, dried with anhydrous magnesium sulfate. The dried extract was filtrated and removed solvent under reduced pressure to provide yellow solid. The crude product was recrystallized from benzene/petroleum ether to give 35.3 g pale yellow crystalline solid in a yield of 85%. $^1$H-NMR (ppm) δ: 9.90 (1H, s; —CHO); 7.32 (1H, m; 2-Ar—H); 7.27 (1H, m; 6-ArH); 6.89 (1H, m; 5-ArH); 4.88 (1H, br; —OH); 4.17 (2H, q; —CH$_2$); 1.53 (3H, t; —CH$_3$). $^{13}$C-NMR (ppm) δ: 192.0 (CHO), 157.6 (4-ArC), 143.3 (3-ArC), 129.6 (1-ArC), 124.5 (6-ArC), 116.7 (2-ArC), 116.6 (5-ArC), 82.1 (—OCH$_2$), 23.5 (—CH$_3$). MS (m/Z): 166 (M$^+$).

Example 4

Synthesis of (Z)-1-(3,4,5-trimethoxy)phenyl-2-(3'-hydroxy-4'-ethoxy) Phenylethylene (Ethoxy Combretastatin)

Step 1: In argon atmosphere, 11.0 g 4-ethoxy-3-hydroxybenzaldehyde (0.066 mol), 21.1 g triphenylmethyl chloride (0.076 mol) and 42 ml dried THF were charged into 500 ml four-necked flask. The mixture was stirred until uniformly. 1.3 ml triethylamine was slowly dropped into the mixture and stirred for 1 hour after addition. The reaction was monitored with TLC. After the reaction completed, 50 ml water was added to quench the reaction. The mixture was stirred another 30 min and 100 ml ethyl acetate was added to dissolve the flocculent precipitate. 250 ml n-heptane was added to precipitate the pale yellow solid. The solid was filtered and was washed twice with water, and then washed with ethyl acetate/petroleum ether (10 ml/20 ml) to give milky white crystal-like solid. Then the solid was recrystallized from ethyl acetate/petroleum ether to give 25 g white crystalline of large particles in a yield of 93%. $^1$H-NMR (ppm) δ: 9.91 (1H, s;

—CHO), 7.33 (1H, m; 2-ArH), 7.26 (1H, m; 6-ArH), 7.19 (15H, m; Tr-H); 6.89 (1H, s, 5-ArH); 4.17 (2H, q; —CH$_2$); 1.53 (3H, t; —CH$_3$).

Step 2: In argon atmosphere, 15 g trimethoxyphenylmethylene triphenylphosphonium bromide (28.7 mmol) was suspended in 300 ml THF, and the mixture was cooled to about −15° C. A 22 ml n-butyl lithium solution in hexane (approximately 1.6 mol/L) was added slowly dropwise, and then the reaction mixture was stirred for another 1 hour. A solution of 11.8 g above-prepared aldehyde (29 mmol) dissolved in 24 ml TIE was added slowly dropwise. The reaction mixture was stirred over night, monitored with TLC, and slowly returned to room temperature. The reaction mixture was cooled again to −5° C. the next day, and brine was added to quench the reaction. The organic layer was separated and the solvent was removed. The crude product was purified by flash column chromatography (silica gel column, 4:1 n-hexane/ethyl acetate) to obtain 13.7 g white crystalline in a yield of 83.5%. $^1$H-NMR (ppm) δ: 7.12 (15H, m; Tr-H); 6.97 (1H, d; 2'-H); 6.81 (1H, dd; 6'-H); 6.75 (1H, d; 5'-H); 6.59 (2H, s; 2, 6-H); 6.47 (1H, d; 1a-H); 6.41 (1H, d; J=12 Hz; 1a'-H); 4.13 (2H, q; —CH$_2$); 3.88 (3H, s; 4-OCH$_3$); 3.71 (6H, s; 3.5-OCH$_3$); 1.55 (3H, t; —CH$_3$).

Step 3: At room temperature, 9.6 g above product via Wittig reaction (16.8 mmol) in step 2 was dissolved in 20 ml toluene. 4 ml 37% aqueous hydrochloric solution (containing 0.2 ml trifluoroacetic acid) was added dropwise. The reaction was monitored with TLC. After the reaction was completed, water was added to stop the reaction. The reaction mixture was cooled to 0-5° C. to recrystallize under agitation. The solid was filtered and dried to give 5.1 g white crystalline in a yield of 92%. $^1$H-NMR (ppm) δ: 7.02 (1H, d; 2'-H); 6.94 (1H, dd; 6'-H); 6.80 (1H, d; 5'-H); 6.62 (2H, s; 2.6-H); 6.46 (1H, d; J=12 Hz; 1a-H); 6.40 (1H, d; J=12 Hz; 1a'-H); 5.51 (1H, br; OH); 4.16 (2H, q; —CH$_2$); 3.86 (3H, s; 4-OCH$_3$); 3.70 (6H, s; 3.5-OCH$_3$); 1.52 (3H, t; —CH$_3$). MS (m/Z): 330 (M$^+$). High resolution mass spectrometry: calcd 330.15, found 330.16.

Example 5

Synthesis of (Z)-1-(3,4,5-trimethoxy)phenyl-2-(3'-amino-4'-ethoxy) Phenylethylene (3'-amino Ethoxy Combretastatin)

Step 1: In photochemical synthesizer with argon atmosphere, 15 g trimethoxyphenylmethylene triphenylphosphonium bromide (28.7 mmol) was suspended in 300 ml THF, and the mixture was cooled to about −15° C. A 22 ml n-butyl lithium solution in hexane (approximately 1.6 mol/L) was slowly dropped into the suspension, and then the reaction mixture was stirred for another 1 hour. Afterward, the 254 nm ultraviolet light was turned on, and a solution of 5.7 g 4-ethoxy-3-nitrobenzaldehyde (29 mmol) in 24 ml THF was slowly dropped into the reaction mixture under the UV radiation. The reaction mixture was monitored with TLC, stirred overnight, and slowly returned to room temperature. The light was turned off the next day, and the reaction mixture was cooled again to −5° C., followed by adding brine to quench the reaction. The organic layer was separated and the solvent was removed by flash distillation. The crude product was purified by normal pressure column chromatography (silica gel column, 4:1 n-hexane/ethyl acetate) to obtain 6.5 g pale yellow crystalline in a yield of 64%. $^1$H-NMR (ppm) δ: 7.32 (1H, d; 2'-H); 7.16 (1H, dd; 6'-H); 6.90 (1H, d; 5'-H); 6.64 (2H, s; 2.6-H); 6.49 (1H, d; J=12.2 Hz); 6.43 (1H, d; J=12.2 Hz); 4.18 (2H, q; —CH$_2$); 3.86 (3H, s; 4-OCH$_3$); 3.70 (6H, s; 3.5-OCH$_3$); 1.55 (3H, t; —CH$_3$). MS (m/Z): 359 (M$^+$). High resolution mass spectrometry: calcd 359.14, found 359.13.

Step 2: 4.1 g (Z)-1-(3,4,5-trimethoxy)phenyl-2-(3'-nitro-4'-ethoxy)phenylethylene (10.8 mmol) was dissolved in 350 ml acetic acid, and 100 g zinc powder (<10 μm) was added. The mixture was stirred for 6 hours. After the reaction was stopped, the mixture was filtered with Buchner funnel paved by 1 cm diatomite, and the filtrate was condensed with rotary evaporator. Then the crude product was purified by flash chromatography (4:1 n-hexane/ethyl acetate), and then recrystallized from about 9:1 n-hexane/ethyl acetate to obtain 2.7 g colorless crystalline in a yield of 77%. $^1$H-NMR (ppm) δ: 7.08 (1H, d; 2'-H); 6.92 (1H, dd; 6'-H); 6.76 (1H, d; 5'-H); 6.62 (2H, s; 2.6-H); 6.49 (1H, d; J=12.2 Hz; 1a-H); 6.43 (1H, d; J=12.2 Hz; 1a'-H); 4.73-4.25 (2H, br; NH$_2$); 4.18 (2H, q; —CH$_2$); 3.86 (3H, s; 4-OCH$_3$); 3.70 (6H, s; 3.5-OCH$_3$); 1.55 (3H, t; —CH$_3$). MS (m/Z): 329 (M$^+$). High resolution mass spectrometry: calcd 329.16, found 329.18.

Example 6

Synthesis of Ethoxy Combretastatin Phosphate Disodium Salt

Step 1: In argon atmosphere, a 1000 ml four-neck flask was charged with 41.6 g ethoxy combretastatin (126 mmol) dissolved in 400 ml dry acetonitrile. The mixture was cooled to −25° C., and was added 61 ml carbon tetrachloride. The mixture was stirred for 5 min, followed by adding 47 ml diisopropylethylamine and 1.5 g 4-dimethylaminopyridine (DMAP). 1 min later, the reaction was slowly added 41 ml dibenzyl phosphite (80%), maintaining temperature lower than −10° C. for another 3.5 hours. The reaction was monitored with TLC. When the reaction completed, 100 ml 0.5M KH$_2$PO$_4$ was added, and the temperature of the reaction returned naturally to room temperature. The mixture was extracted with ethyl acetate, and the organic layer was collected, washed with distilled water and brine successively, dried with anhydrous magnesium sulfate, distilled under reduced pressure to remove solvents, obtaining opaque oily product. The crude product was purified by flash column (silica gel, 3:2 petroleum ether/ethyl acetate) to give 75 g oily product in pale yellow, and then recrystallized from n-hexane/ethyl acetate to obtain 68.4 g colorless needle-like crystalline in a yield of 92%.

Step 2: In argon atmosphere, a 1000 ml four-neck flask was charged with 65 g above dried benzyl phosphate (110 mmol) dissolved in 250 ml dry acetonitrile at 15° C. The mixture was stirred and added 45 ml trimethylbromosilane (TMBS) quickly. After 5-10 min, 18 g sodium methoxide dissolved in 70 ml anhydrous methanol was added, and the mixture turned to milky white suspension instantly. Half an hour later, the reaction was added 36 ml anhydrous methanol, 36 ml acetone, stirred overnight. The mixture was filtered to obtain white solid, which was then washed by anhydrous methanol and acetone, dried in vacuum. The solid was recrystallized from water/methanol/acetone to give 43 g white powder in a yield of 86%. $^1$H-NMR (ppm) δ: 7.11 (1H, d; 2'-H); 6.98 (1H, dd; 6'-H); 6.87 (1H, d; 5'-H); 6.64 (2H, s; 2.6-H); 6.47 (1H, d; J=12 Hz; 1a-H); 6.42 (1H, d; J=12 Hz; 1a'-H); 4.18 (2H, q; —CH$_2$); 3.86 (3H, s; 4-OCH$_3$); 3.70 (6H, s; 3.5-OCH$_3$); 1.52

(3H, t; —CH$_3$). MS (m/Z): 454 (M$^+$). High resolution mass spectrometry: calcd 454.08, found 454.06.

Example 7

Synthesis of Inner Salt of Ethoxy Combretastatin Phosphorylcholine

Step 1: A dried 500 ml three-neck flask was charged with a solution of 68 g dry phosphorous trichloride (0.5 mol) in 100 ml dichloromethane. The mixture was cooled to keep 0° C., and a solution of 31 g dry ethylene glycol (0.5 mol) in 100 ml dichloromethane was added dropwise. After that, the reaction mixture was allowed to return room temperature and continued reacting for 3 hours. Then the solvent was removed, and the residue was distilled under reduced pressure to collect fraction at 60° C./20 mmHg, obtaining 41 g 2-chloro-1,3,2-dioxaphospholane in a yield of 65%. $^1$H-NMR (CDCl$_3$, 500M) δ: 4.46 (2H, m; a-CHCH—); 4.24 (2H, m, e-CHCH—).

Step 2: A 100 ml three-neck flask was charged with 50 ml anhydrous benzene and 25.3 g 2-chloro-1,3,2-dioxaphospholane (0.2 mol), slowly purging oxygen into the solution. After about one-hour of purging oxygen, the mixture was heated to reflux and maintained for 5-6 hours. Then the reaction was cooled to room temperature, the solvent was removed, and the residue was distilled under reduced pressure to collect fraction at 90° C./1 mmHg, obtaining 12.3 g 2-chloro-1,3,2-dioxaoxidophospholane in a yield of 43%. $^1$H-NMR (CDCl$_3$, 500M) δ: 4.64 (2H, m; a-CHCH—); 4.56 (2H, m, e-CHCH—).

Step 3: In argon atmosphere, 3.3 g ethoxy combretastatin (10 mmol) and 1.0 g triethylamine (10 mmol) were dissolved in 20 ml dry benzene. The mixture was cooled to −40° C., and added a solution of 1.42 g 2-chloro-1,3,2-dioxaoxidophospholane (10 mmol) dissolved in 20 ml benzene dropwise under stirring. After that, the reaction was kept for half an hour, and then returned to room temperature, stirred for another 10 hours. Afterwards, the mixture was filtered to remove triethylamine hydrochloride, and the filtrate was distilled to remove part of the solvent. The residue was washed by 15 ml 15% sodium carbonate, extracted by 50 ml diethyl ether, followed by extracting the water layer again with 50 ml diethyl ether. The ether layer was collected, washed with 10% sodium carbonate (20 ml×2), dried, filtered, and distilled to remove diethyl ether, obtaining 3.5 g solid phosphate in pale yellow in a yield of 81%. The above phosphate was then dissolved in 50 ml acetonitrile, followed by adding 5 ml trimethylamine aqueous solution (28%), stirred for 20 hours at room temperature, and monitored with TLC. After the reaction completed, the mixture was added 50 ml acetone, cooled to −30° C., stirred to give crystalline, then filtered, dried to obtain white crude product. The crude product was recrystallized from 95% ethanol to give 3 g white crystalline in a yield of 76%. $^1$H-NMR (ppm) δ: 7.27 (1H, d; 2'-H); 6.63 (1H, dd; 6'-H); 6.51 (1H, d; 5'-H); 6.46 (1H, d; 1a-H); 6.380 (2H, s; 2.6-H); 6.20 (1H, d; 1a'-H); 4.62 (2H, m; a-CHCH—); 4.53 (2H, m, e-CHCH—); 4.18 (2H, q; —OCH$_2$); 3.86 (3H, s; 4-OCH$_3$); 3.70 (6H, s; 3.5-OCH$_3$); 3.18 (9H, s; NMe$_3$); 1.52 (3H, t; —CH$_3$). MS (m/Z): 495 (M$^+$). High resolution mass spectrometry: calcd 495.20, found 495.22.

Example 8

Synthesis of 3'-amino Ethoxy Combretastatin Glycinamide

Step 1: 4.28 g 3'-amino ethoxy combretastatin (13 mmol), 4.75 g Fmoc-glycine (16 mmol), and 22.7 g BOP reagent (51.6 mmol) were dissolved in 100 ml DMF. The mixture was heated to 60° C., and reacted for 2 hours under stirring. The reaction was monitored with TLC. After the reaction completed, it was cooled and well-mixed with 100 ml saturated sodium bicarbonate solution. Then the mixture was extracted with dichloromethane (120 ml×3), and the organic layer was dried on anhydrous magnesium sulfate and condensed under reduced pressure. The resulting crude product was then purified by flash column chromatography (silica gel column, 2:1 n-hexane/ethyl acetate) to obtain 3.3 g white foamy substance in a yield of 42%. $^1$H-NMR (CDCl$_3$, 500M) δ: 9.61 (1H, brs; —NH); 7.74 (2H, m; Fmoc); 7.59 (2H, d; J=6.2 Hz; Fmoc); 7.37 (2H, m; Fmoc); 7.29 (2H, m; Fmoc); 7.08 (1H, d; 2'-H); 6.92 (1H, dd; 6'-H); 6.76 (1H, d; 5'-H); 6.62 (2H, s; 2.6-H); 6.49 (1H, d; J=12.2 Hz; 1a-H); 6.43 (1H, d; J=12.2 Hz; 1a'-H); 5.79 (1H, brs; Gly-NH); 4.38 (2H, d; J=7.0 Hz; Fmoc); 4.22 (1H, t; J=7.0 Hz; Fmoc); 4.18 (2H, q; —CH$_2$); 4.04 (2H, m; Gly-CH$_2$); 3.86 (3H, s; 4-OCH$_3$); 3.70 (6H, s; 3.5-OCH$_3$); 1.55 (3H, t; —CH$_3$). MS (m/Z): 608 (M$^+$). High resolution mass spectrometry: calcd 608.25, found 608.27.

Step 2: 2.2 g above (Z)-1-(3,4,5-trimethoxy)phenyl-2-(3'-amino-4'-ethoxy)phenylethylene Fmoc-glycinamide (3.6 mmol) was dissolved in 40 ml methanol. The solution was added 2 ml 2N sodium hydroxide solution, and reacted for 3 hours under stirring at room temperature. The reaction was monitored with TLC. After the reaction completed, it was cooled and well-mixed with 20 ml saturated sodium bicarbonate solution. Then the mixture was extracted with dichloromethane (50 ml×3), and the organic layer was dried with anhydrous magnesium sulfate and condensed under reduced pressure. The obtained crude product was then purified by normal pressure column chromatography (silica gel column, 9:1 dichloromethane/methanol) to obtain 0.97 g colorless foamy substance in a yield of 70%. $^1$H-NMR (CDCl$_3$, 500M) δ: 9.61 (1H, brs; —NH); 7.08 (1H, d; 2'-H); 6.92 (1H, dd; 6'-H); 6.76 (1H, d; 5'-H); 6.62 (2H, s; 2.6-H); 6.49 (1H, d; J=12.2 Hz; 1a-H); 6.43 (1H, d; J=12.2 Hz; 1a'-H); 4.81-4.32 (2H, br; Gly-NH$_2$); 4.18 (2H, q; —CH$_2$); 4.04 (2H, brs; Gly-CH$_2$); 3.86 (3H, s; 4-OCH$_3$); 3.70 (6H, s; 3.5-OCH$_3$); 1.55 (3H, t; —CH$_3$). MS (m/Z): 386 (M$^+$). High resolution mass spectrometry: calcd 386.18, found 386.20.

Example 9

Synthesis of 3'-amino Ethoxy Combretastatin Serinamide

Step 1: 4.28 g 3'-amino ethoxy combretastatin (13 mmol), 5.89 g Fmoc-serine (16 mmol), 3.37 g DCC (16 mmol), and 2.44 g HOBt were dissolved in 80 ml DMF. The mixture was reacted for 5 hours under stirring at room temperature, and monitored with TLC. After the reaction completed, it was cooled and well-mixed with 50 ml ethyl acetate to dilute the mixture. Then the mixture was filtered, dried with anhydrous magnesium sulfate and condensed under reduced pressure. The obtained crude product was then purified by flash column chromatography (silica gel column, 2:1 n-hexane/ethyl acetate) to obtain 5.1 g white foamy substance in a yield of 61%. $^1$H-NMR (CDCl$_3$, 500M) δ: 9.73 (1H, brs; —NH); 7.73 (2H, m; Fmoc); 7.56 (2H, d; J=6.2 Hz; Fmoc); 7.35 (2H, m;

Fmoc); 7.22 (2H, m; Fmoc); 7.05 (1H, d; 2'-H); 6.91 (1H, dd; 6'-H); 6.74 (1H, d; 5'-H); 6.60 (2H, s; 2.6-H); 6.51 (1H, d; J=12.2 Hz; 1a-H); 6.43 (1H, d; J=12.2 Hz; 1a'-H); 5.82 (1H, brs; Ser-NH); 4.63 (1H, brs; Ser-OH); 4.38 (2H, d; J=7.0 Hz; Fmoc); 4.22 (1H, t; J=7.0 Hz; Fmoc); 4.18 (2H, q; —CH$_2$); 3.91 (1H, m; Ser-CH); 3.85 (3H, s; 4-OCH$_3$); 3.71 (6H, s; 3.5-OCH$_3$); 2.66 (2H, m; Ser-CH$_2$); 1.56 (3H, t; —CH$_3$). MS (m/Z): 638 (M$^+$). High resolution mass spectrometry: calcd 638.26, found 638.27.

Step 2: 1.9 g above (Z)-1-(3,4,5-trimethoxy)phenyl-2-(3'-amino-4'-ethoxy)phenylethylene Fmoc-serinamide (3.0 mmol) was dissolved in mixed solvents consisting of 20 ml methanol and 20 ml dichloromethane. To the solution was added 3.4 ml 2N sodium hydroxide solution, and reacted for 24 hours at room temperature under stirring. The reaction was monitored with TLC. After the reaction completed, it was cooled and well-mixed with 20 ml saturated sodium chloride solution. Then the mixture was extracted with dichloromethane (50 ml×3), and the organic layer was dried with anhydrous magnesium sulfate and condensed under reduced pressure. The resulting crude product was then purified by normal pressure column chromatography (silica gel column, 9:1 dichloromethane/methanol) to obtain 0.62 g colorless foamy substance in a yield of 50%. $^1$H-NMR (CDCl$_3$, 500M) δ: 9.75 (1H, brs; —NH); 7.08 (1H, d; 2'-H); 6.94 (1H, dd; 6'-H); 6.75 (1H, d; 5'-H); 6.63 (2H, s; 2.6-H); 6.53 (1H, d; J=12.2 Hz; 1a-H); 6.45 (1H, d; J=12.2 Hz; 1a'-H); 5.51-4.72 (2H, br; Ser-NH$_2$); 4.52 (1H, brs; Ser-OH); 4.19 (2H, q; —CH$_2$); 3.92 (1H, m; Ser-CH); 3.86 (3H, s; 4-OCH$_3$); 3.72 (6H, s; 3.5-OCH$_3$); 2.68 (2H, m; Ser-CH$_2$); 1.57 (3H, t; —CH$_3$). MS (m/Z): 416 (M$^+$). High resolution mass spectrometry: calcd 416.19, found 416.20.

Comparative Example

Synthesis of Propoxy Combretastatin

This example was according to Example 1, except that ethyl bromide with replaced by propyl bromide to prepare 4-propoxy-3-methoxy benzaldehyde. Then according to Example 3 and 4, propoxy combretastatin was obtained. $^1$H-NMR (ppm) δ: 7.02 (1H, d; 2'-H); 6.94 (1H, dd; 6'-H); 6.80 (1H, d; 5'-H); 6.62 (2H, s; 2.6-H); 6.46 (1H, d; J=12 Hz; 1a-H); 6.40 (1H, d; J=12 Hz; 1a'-H); 5.51 (1H, br; OH); 4.16 (2H, q; —CH$_2$); 3.86 (3H, s; 4-OCH$_3$); 3.70 (6H, s; 3.5-OCH$_3$); 2.27 (2H, m; —CH$_2$); 1.18 (3H, t; —CH$_3$). MS (m/Z): 344 (M$^+$). High resolution mass spectrometry: calcd 344.18, found 344.16.

Example 10

In Vitro Anti-Tumor Activity Evaluation

The tumor cell cultured in vitro was treated with ethoxy combretastatin derivatives for 72 hours, and the MTT and SRB assays was used to evaluate its inhibition of tumor proliferation. The comparative result with CA-4 was shown in Table 2.

Cell Line: H460 (human lung cancer cell), SGC7901 (human stomach cancer cell), HT-29 (human colon cancer cell), Bel-7402 (human liver cancer cell).

Experimental Design: The cells were incubated with the compounds in various concentrations (100, 10, 1, 0.1, 0.01, 0.001 μM) for 72 hours. SRB assay was used to evaluate the inhibition effect of the compounds on cell proliferation. The inhibition rate was calculated, and IC$_{50}$ was calculated by using Logit model as a function of the inhibition rate. And the anti-tumor activity of the compounds in vitro was compared.

The Inhibition Rate was Expressed Using the Following Equation:

$$\text{Inhibition rate (\%)}=[(\text{average } OD \text{ value of control group}-\text{average } OD \text{ value of experimental group})/\text{average } OD \text{ value of control group}]\times 100\%.$$

| | IC$_{50}$ (μM) | | | |
|---|---|---|---|---|
| Comd. | Stomach cancer SGC-7901 | Non-small cell lung cancer H460 | Colon cancer HT29 | Liver cancer Bel-7402 |
| CA-4 | 0.010 | 0.027 | 2.380 | 0.75 |
| Ethoxy combretastatin | 0.008 | 0.011 | 0.047 | 0.62 |
| 3'-Amino ethoxy combretastatin | 0.006 | 0.008 | 0.025 | 0.33 |
| Propoxy combretastatin | 6.563 | 7.811 | >20 | 10.532 |

The result showed that all of the ethoxy combretastatins derivatives had more effective anti-tumor activity in vitro than that of natural Combretastatin A-4 in different kind of cancer cell lines. Specifically, the ethoxy combretastatins had 50 to 95 folds of anti-tumor activity than that of Combretastatin A-4 in colon cancer cells, while propoxy combretastatin, the product obtained in the comparative example, showed little anti-cancer activity.

Example 11

In Vitro Neovascular Inhibition Evaluation

Anti-angiogenesis effects of ethoxy combretastatins were assessed in human umbilical vein endothelial cells (HUVEC) using the same method described in Example 10.

| Comd. | IC$_{50}$ (μM) HUVEC |
|---|---|
| CA-4 | 3.7 |
| Ethoxy combretastatin | 2.2 |
| 3'-Amino ethoxy combretastatin | 1.5 |
| Propoxy combretastatin | >3000 |

The result showed that ethoxy combretastatins had strong tubulin-binding inhibition activity, and indicated that ethoxy combretastatins were a new class of potential tumor vascular targeting drugs. While propoxy combretastatin, the product obtained in the comparative example, hardly showed this kind of activity.

Example 12

Preparation of Ethoxy Combretastatins Freeze-Dried Powder

| Formula | Content (g) |
| --- | --- |
| Ethoxy combretastatin phosphate disodium salt in Example 6 | 25 |
| Mannitol | 125 |
| Injection water | 2500 |
| DD8031DP freeze-dried powder | 0.025/bottle × 1000 bottle |

Materials were weighed exactly according to the formulas (Table 4). Formula amount of mannitol was dissolved in 80% of the total formula amount of injection water to give a clarity solution, and 0.1% (g/ml) injection active carbon was added. The mixture was stirred until uniformity, settled for about 10 min, and filtered through 0.45 μm micropore membrane. The rest amount of the injection water was added. The solution was filtered again through 0.22 μm micropore membrane. pH value and content were measured to give the qualified product. And then, a quantity of the solution was filled into bottles and was freeze dried. The bottles were filled with nitrogen and then cap-covered and labeled. They were packaged into boxes, and proof-tested to give finished product (because the derivatives of Combretastatin were moderately sensitive to temperature and light, so the whole operation processes were done in dark condition).

All the documents cited herein are incorporated into the invention as reference, as if each of them is individually incorporated. Further, it would be appreciated that, in the above teaching of invention, the skilled in the art could make certain changes or modifications to the invention, and these equivalents would still be within the scope of the invention defined by the appended claims of the application.

What is claimed is:

1. A compound of formula (I) or its pharmaceutically acceptable salts:

wherein R is hydroxyl, amino, disodium or ammonium phosphate, or inner salt of phosphorylcholine, —NH(COCHR'NH)$_m$—H; wherein R' is hydrogen, side chain of a natural amino acid, phenyl; m is an integer of 1 to 3.

2. The compound of claim 1, wherein R is selected from —OH, —NH$_2$, —OPO$_2$Na$_2$, —OPO$_3$CH$_2$CH$_2$NMe$_3$, —NHCOCH$_2$NH$_2$, or —NHCOCHNH$_2$CH$_2$OH.

3. A method for preparing the compound of claim 1, wherein R is phosphate or inner salt of phosphorylcholine, the method comprising the steps of: (1) under phase-transfer catalyst conditions, 4-hydroxy-3-methoxybenzaldehyde II is ethylated with ethyl bromide to synthesize 4-ethoxy-3-methoxybenzaldehyde represented by formula III;

(2) using lithium diphenylphosphine, selectively replacing m-methyl of 4-ethoxy-3-methoxybenzaldehyde III with hydroxyl to synthesize 4-ethoxy-3-hydroxybenzaldehyde represented by formula IV;

(3) with hydroxyl being protected, 4-ethoxy-3-hydroxybenzaldehyde IV is reacted with 3,4,5-trimethoxybenzyltriphenylphosphonium ylid via Wittig reaction, and then the resulting compound is deprotected to obtain ethoxy combretastatin represented by formula VI;

(4) ethoxy combretastatin VI is phosphorylated with phosphoryl reagent to synthesize its phosphate derivatives; and (5) under alkaline conditions, phosphate derivatives of ethoxy combretastatin are converted to ethoxy combretastatin phosphate or inner salt of phosphorylcholine.

4. The method of claim 3, wherein the phosphoryl reagent in step (4) is selected from dibenzyl phosphite or 2-chloro-1,3,2-dioxaphospholane.

5. A method for preparing the compound of claim 1, wherein R is amino, —NH(COCHR'NH)$_m$—H; wherein R' is hydrogen, side chain of a natural amino acid, phenyl; m is an integer of 1 to 3, the method comprising the steps of:

(a) under phase-transfer catalyst conditions, 4-hydroxy-3-nitrobenzaldehyde IX is ethylated with ethyl bromide to synthesize 4-ethoxy-3-nitrobenzaldehyde represented by formula X;

(b) catalyzed by 254 nm ultraviolet light, 4-ethoxy-3-nitrobenzaldehyde X is reacted with 3,4,5-trimethoxybenzyltriphenylphosphine ylid via Wittig reaction to obtain (Z)-1-(3,4,5-trimethoxy)phenyl-2-(3'-nitro-4'-ethoxy)phenylethylene represented by formula XI;

(c) (Z)-1-(3,4,5-trimethoxy)phenyl-2-(3'-nitro-4'-ethoxy)phenylethylene XI is reduced with reducing agents to give 3'-amino ethoxy combretastatin XII;

(d) 3'-amino ethoxy combretastatin XII is reacted with amino acid derivatives to give corresponding amino amide derivatives; and
(e) under alkaline conditions, the above mentioned amino amide derivatives are converted to 3'-amino ethoxy combretastatin amino amides.

6. A pharmaceutical composition for treating a tumor and/or a pathological state caused by abnormal angiogenesis comprising a therapeutically effective amount of the compound of claim 1 and pharmaceutically acceptable carrier.

7. A method of treatment of patients with a tumor, comprising the administration to said patient of the compound in accordance with claim 1 or a pharmaceutically acceptable salt thereof.

8. A method of treatment of patients with a pathological state caused by abnormal angiogenesis, comprising the administration to said patient of the compound in accordance with claim 1 or a pharmaceutically acceptable salt thereof.

9. A method for preparing the compound of claim 2, wherein R is phosphate or inner salt or phosphorylcholine, the method comprising the steps of:
(1) under phase-transfer catalyst conditions, 4-hydroxy-3-methoxybenzaldehyde II is ethylated with ethyl bromide to synthesize 4-ethoxy-3-methoxybenzaldehyde represented by formula III;

(2) using lithium diphenylphosphine, selectively replacing m-methyl of 4-ethoxy-3-methoxybenzaldehyde III with hydroxyl to synthesize 4-ethoxy-3-hydroxybenzaldehyde represented by formula IV;

(3) with hydroxyl being protected, 4-ethoxy-3-hydroxybenzaldehyde IV is reacted with 3,4,5-trimethoxybenzyltriphenylphosphonium ylid via Wittig reaction, and then the resulting compound is deprotected to obtain ethoxy combretastatin represented by formula VI;

(4) ethoxy combretastatin VI is phosphorylated with phosphoryl reagent to synthesize its phosphate derivatives; and
(5) under alkaline conditions, phosphate derivatives of ethoxy combretastatin are converted to ethoxy combretastatin phosphate or inner salt of phosphorylcholine.

* * * * *